(12) United States Patent
Tanigawa et al.

(10) Patent No.: US 11,110,371 B2
(45) Date of Patent: Sep. 7, 2021

(54) PROTEIN CRYSTALLIZATION METHOD AND CRYSTALLIZATION DEVICE

(71) Applicants: CHIYODA CORPORATION, Kanagawa (JP); CONFOCAL SCIENCE INC., Tokyo (JP)

(72) Inventors: Naoki Tanigawa, Kanagawa (JP); Hiroaki Tanaka, Tokyo (JP); Sachiko Takahashi, Tokyo (JP); Koji Inaka, Nara (JP)

(73) Assignees: CHIYODA CORPORATION, Kanagawa (JP); CONFOCAL SCIENCE INC., Tokyo (JP)

( * ) Notice: Subject to any disclaimer, the term of this patent is extended or adjusted under 35 U.S.C. 154(b) by 138 days.

(21) Appl. No.: 16/489,510

(22) PCT Filed: Dec. 27, 2017

(86) PCT No.: PCT/JP2017/046880
§ 371 (c)(1),
(2) Date: Aug. 28, 2019

(87) PCT Pub. No.: WO2018/159089
PCT Pub. Date: Sep. 7, 2018

(65) Prior Publication Data
US 2020/0070064 A1 Mar. 5, 2020

(30) Foreign Application Priority Data
Mar. 2, 2017 (JP) .............................. JP2017-039143

(51) Int. Cl.
*C30B 29/58* (2006.01)
*B01D 9/00* (2006.01)
(Continued)

(52) U.S. Cl.
CPC .......... *B01D 9/005* (2013.01); *B01D 9/0077* (2013.01); *B01D 61/362* (2013.01);
(Continued)

(58) Field of Classification Search
CPC .. C30B 7/04; C30B 7/14; C30B 29/54; C30B 29/58
See application file for complete search history.

(56) References Cited

U.S. PATENT DOCUMENTS 5,104,478 A * 4/1992 Sikdar ...................... C30B 7/00
117/70
10,365,188 B2 * 7/2019 Fraden ..................... C12M 3/00
(Continued)

FOREIGN PATENT DOCUMENTS

JP 2004-026528 1/2004
JP 2004-045169 2/2004
(Continued)

OTHER PUBLICATIONS

International Search Report dated Apr. 3, 2018 in International Application No. PCT/JP2017/046880.

*Primary Examiner* — Robert M Kunemund
(74) *Attorney, Agent, or Firm* — Wenderoth, Lind & Ponack, L.L.P.

(57) ABSTRACT

Provided are: an economically superior protein crystallization method capable of efficiently finding conditions for crystallization by using a small amount of protein; and a crystallization device used for the method. According to the present invention, a transparent sealed container 1 is filled with a solution of protein, a part of the transparent sealed container 1 being formed of a semipermeable membrane 2 with a molecular weight cut-off that inhibits passage of the protein while allowing passage of a precipitant, and then, a precipitant solution with changed concentration and/or pH of the precipitant is continuously supplied to the semiper- (Continued)

meable membrane 2, to crystallize the protein with the precipitant that infiltrates from the semipermeable membrane 2 into the sealed container 1.

8 Claims, 2 Drawing Sheets

(51) Int. Cl.
*B01D 61/36* (2006.01)
*C12N 9/36* (2006.01)

(52) U.S. Cl.
CPC .... *C12N 9/2462* (2013.01); *C12Y 302/01017* (2013.01); *B01D 2009/0086* (2013.01); *B01D 2311/12* (2013.01); *B01D 2311/2642* (2013.01)

(56) References Cited

U.S. PATENT DOCUMENTS

| | | |
|---|---|---|
| 2003/0233978 A1 | 12/2003 | Niimura et al. |
| 2004/0033166 A1* | 2/2004 | Arnowitz ............... C30B 7/00 422/82.05 |
| 2007/0072281 A1* | 3/2007 | Rummel ............... A61P 37/08 435/194 |
| 2016/0318974 A1* | 11/2016 | Kubicek ............... B01D 9/00 |

FOREIGN PATENT DOCUMENTS

| | | |
|---|---|---|
| JP | 2006-83126 | 3/2006 |
| JP | 2006-281139 | 10/2006 |
| WO | 2002/026342 | 4/2002 |

* cited by examiner

PROTEIN CRYSTALLIZATION METHOD AND CRYSTALLIZATION DEVICE

TECHNICAL FIELD

The present invention relates to a protein crystallization method and a protein crystallization device, which crystallize protein by continuously supplying a precipitant solution with a changed concentration through a semipermeable membrane.

BACKGROUND ART

In recent years, for example, in the pharmaceutical industry and the like, protein has been crystallized and analyzed by techniques such as X-ray diffraction and neutron diffraction in order to search protein-binding compounds or to clarify the relationship between the function and structure of the protein in basic research.

Meanwhile, at the time of the protein crystallization, generally, a method has been widely adopted in which a precipitant is added to a protein solution to lower the solubility of the solution and precipitate the protein. However, the concentration of the precipitant at the time of the protein crystallization and the pH thereof during the reaction vary depending on the type of the protein.

Therefore, for finding precise crystallization conditions for the protein, for example, as seen in Patent Document 1 mentioned below, a method has been hitherto been widely adopted in which a large number of samples with changed concentrations and/or pHs of the precipitant are previously prepared and screening is comprehensively performed to grasp the crystallization conditions, and a reagent kit for the method has also been proposed as seen in Patent Document 2 mentioned below.

CITATION LIST

Patent Literature

Patent Literature 1: Japanese Patent Laid-Open No. 2006-281139
Patent Literature 2: Japanese Patent Laid-Open No. 2006-083126

SUMMARY OF INVENTION

Technical Problem

However, the above method to find the protein crystallization conditions by screening has the problem of requiring a great deal of time and effort since comprehensive screening is performed using a large number of samples. In addition, the method also has the problem of being economically inferior since a large amount of valuable protein also needs to be prepared.

The present invention has been made in view of the above circumstances, and an object of the present invention is to provide an economically superior protein crystallization method capable of efficiently finding conditions for crystallization by using a small amount of protein and also provide a crystallization device used for the method.

Solution to Problem

For solving the above problem, a protein crystallization method according to a first aspect of the present invention is characterized by including: filling a transparent sealed container with a solution of protein, a part of the transparent sealed container being formed of a semipermeable membrane with a molecular weight cut-off that inhibits passage of the protein while allowing passage of a precipitant; and continuously supplying a precipitant solution with changed concentration and/or pH of the precipitant to the semipermeable membrane, to crystallize the protein with the precipitant that infiltrates from the semipermeable membrane into the sealed container.

A second aspect of the invention is characterized in that in addition to the first aspect of the invention, dry air or liquid having hygroscopic properties is continuously supplied to a gas permeable membrane disposed in a position that faces the semipermeable membrane of the sealed container and having a molecular weight cut-off that inhibits passage of liquid while allowing passage of water vapor, to form gradients of the concentration and/or pH of the precipitant and a concentration of the protein in the sealed container.

A third aspect of the invention is characterized in that in addition to the first or second aspect of the invention, the solution with which the sealed container is filled contains, in addition to the protein, the precipitant having a concentration with which the protein is not crystallized.

A fourth aspect of the invention is characterized by including: a transparent sealed container filled with a solution containing protein; a semipermeable membrane that forms a part of the sealed container and inhibits passage of the protein while allowing passage of a precipitant; and precipitant supply means that circulates and supplies a precipitant solution containing the precipitant to the semipermeable membrane. The precipitant supply means includes a reservoir that stores the precipitant solution, a circulation line that supplies the precipitant solution in the reservoir to the semipermeable membrane and returns the precipitant solution to the reservoir again, a pump that is disposed on the circulation line and continuously supplies the precipitant solution to the semipermeable membrane, and concentration adjustment means that changes the precipitant concentration in the precipitant solution.

A fifth aspect of the invention is characterized in that in addition to the fourth aspect of the invention, the sealed container is a tubular member having one end closed and the other end formed with an opening, and the semipermeable membrane is formed in a bag-like shape integrated at the opening with a cylindrical narrow tube and is inserted into the sealed container via a sealing member. The sealing member includes a cylindrical elastic member having a hole formed in a center, the hole having a diameter smaller than outer diameters of the sealed container and the narrow tube, and a cylindrical restraint tube having an inner diameter size smaller than an outer diameter size of the elastic member. The sealed container is fitted to one end of the hole in the elastic member while the narrow tube is fitted to the other end of the hole, and the compressed elastic member is fitted into the restraint tube.

A sixth aspect of the invention is characterized by including, in addition to the fourth or fifth aspect of the invention: a gas permeable membrane disposed in a position that faces the semipermeable membrane of the sealed container and having a molecular weight cut-off that inhibits passage of liquid while allowing passage of water vapor; second supply means that continuously supplies dry air or liquid having hygroscopic properties to the gas permeable membrane; and discharge means for water vapor discharged out of the sealed container through the gas permeable membrane.

Further, a seventh aspect of the invention is characterized in that in addition to any one of the fourth to sixth aspects of the invention, the sealed container is made of glass or quartz.

Moreover, an eighth aspect of the invention is characterized in that in addition to the fifth aspect of the invention, the elastic member is silicone rubber with a hardness of 15 degrees to 25 degrees. Note that the hardness is measured by a durometer corresponding to JIS (Japanese Industrial Standard) K 6253.

Advantageous Effects of Invention

According to any one of the first to eighth aspects of the invention, with respect to the solution of protein having filled the transparent sealed container, the precipitant solution with the changed concentration and/or pH of the precipitant is continuously supplied to the semipermeable membrane forming a part of the sealed container, to gradually change the concentration and/or pH of the precipitant infiltrating from the semipermeable membrane into the sealed container and crystallize the protein, so that it is possible to crystallize the protein without changing the concentration of the protein.

Due to the sealed container being transparent, it is possible, by observing the crystallization of the protein from the outside, to grasp conditions of the concentration and/or pH of the precipitant at the time of the protein crystallization from the fact of the protein crystallization and the concentration and/or pH of the precipitant at the time of the crystallization. Therefore, it is possible to efficiently find conditions for the crystallization by using a small amount of protein.

At the time of crystallizing protein by finding the protein crystallization conditions, when the obtained protein crystals are analyzed by neutron diffraction or X-ray diffraction, a larger crystal can be analyzed in more detail. It is thereby preferable to crystallize the protein into a large size of 1 $mm^3$ or more.

However, in general, when the protein is crystallized, the amount of protein forming one protein crystal is small because protein around each of crystal nuclei, generated at many locations in the protein solution, is evenly distributed and crystallized, resulting in that large protein crystals are difficult to generate, which has hitherto been problematic.

In contrast, according to the second or sixth aspects of the invention, by continuously supplying dry air or liquid having hygroscopic properties to the gas permeable membrane disposed in the position that faces the semipermeable membrane of the sealed container and discharging water vapor from the sealed container, a gradient is formed in which the concentration and/or pH of the precipitant are higher on the semipermeable membrane side than on the gas permeable membrane side, and a gradient is formed in which the protein concentration is higher on the gas permeable membrane side than on the semipermeable membrane side. Thereby, a wide range of crystallization conditions are created in the sealed container, and the crystal nuclei are generated in one to several locations, thus enabling the generation of large protein crystals.

For comparison, as in the third aspect of the invention, when the precipitant having a concentration, with which the protein is not crystallized, is previously added besides the protein to the solution filling the sealed container, it is also possible to shorten the operation time until crystallization of the protein.

In the fourth aspect of the invention, the protein crystallization device, as a mode in which a part of the sealed container is formed of the semipermeable membrane, it is possible to adopt the configuration as in the fifth aspect of invention where the bag-like semipermeable membrane is inserted into the sealed container made of a tubular member through its opening, and the space between the sealed container and the narrow tube integrated into the opening of the semipermeable membrane is sealed with a sealing member formed by the restraint tube compressing an elastic member.

At the time of changing the concentration of the precipitant in the sealed container via the semipermeable membrane, when the difference in concentration of the solution between both sides of the semipermeable membrane increases, osmotic pressure occurs and the sealed container is depressurized or pressurized, which may cause air to enter the sealed container or the internal solution to leak. For example, when the concentration difference between the inside and the outside of the semipermeable membrane is 50 mM, the osmotic pressure corresponds to about 1.2 atm.

In this regard, according to the sealing member of the fifth aspect of the invention described above, the narrow tube integrated to the opening end of the sealed container and the semipermeable membrane is fitted to the elastic member, and the elastic member is compressed by the restraint tube, so that by the repulsive force of the elastic member, the spaces between the hole of the elastic member, the opening end of the sealed container, and the outer periphery of the narrow tube are sealed, and the space between the outer periphery of the elastic member and the restraint tube is sealed. Hence it is possible to obtain sealing strength high enough to withstand the difference in osmotic pressure generated between the inside and the outside of the sealed container.

In this case, as the sealed container, glass or quartz is preferably used as in the seventh aspect of the invention in order to inhibit passage of gas such as water vapor into the sealed container.

Further, as the elastic body constituting the sealing member, silicone rubber with a hardness of 15 degrees to 25 degrees as in the eighth aspect of the invention is preferred.

DESCRIPTION OF EMBODIMENTS

First Embodiment

Figure 1:
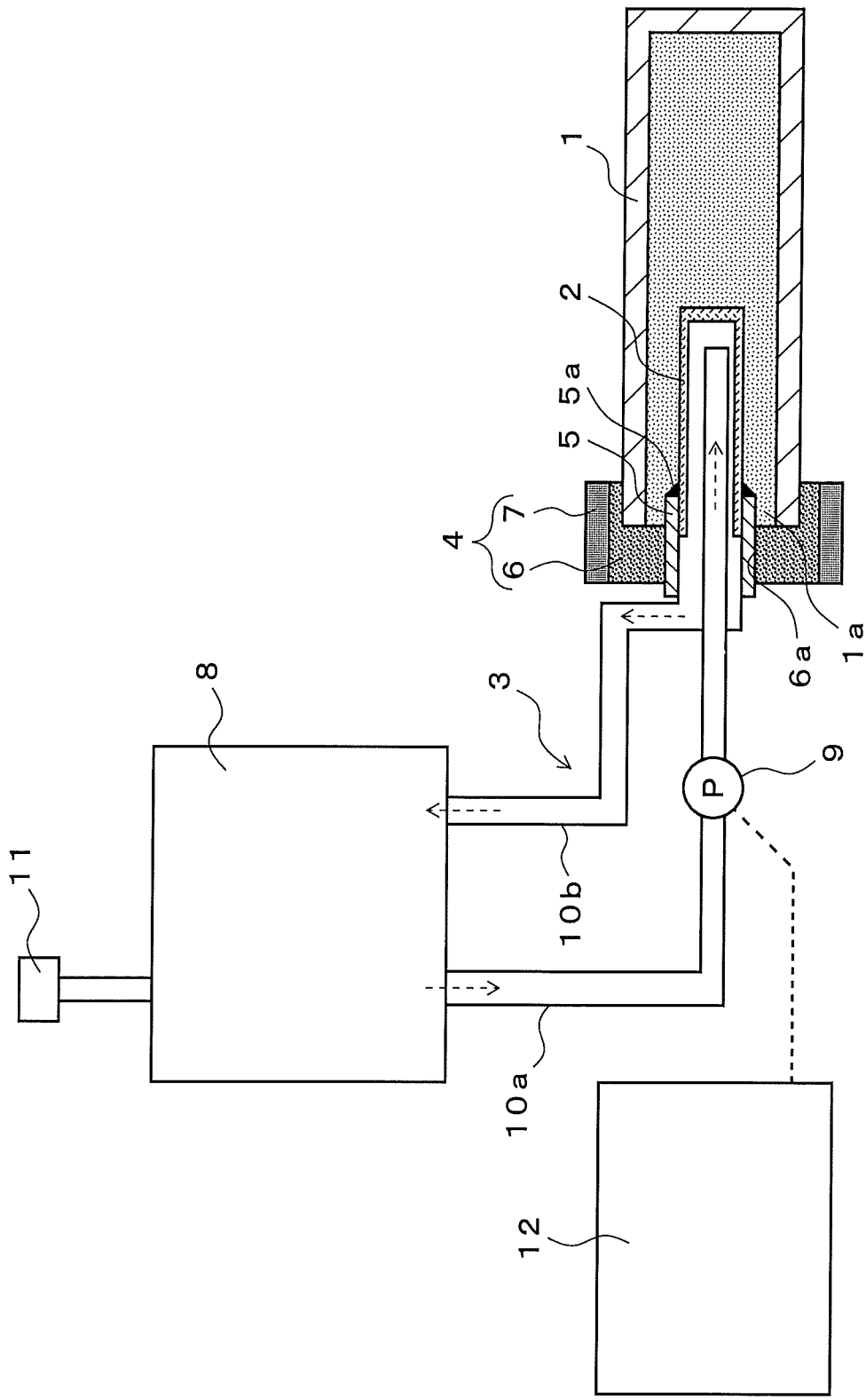
FIG. 1 is a schematic configuration view illustrating a first embodiment of a protein crystallization device according to the present invention.

FIG. 1 illustrates a first embodiment of a protein crystallization device according to the present invention, and the protein crystallization device is roughly configured of: a transparent sealed container 1 that is filled with a solution containing protein; a semipermeable membrane 2 inserted in the sealed container 1; and precipitant supply means 3 that circulates and supplies a precipitant solution containing a precipitant to the semipermeable membrane 2.

The sealed container 1 is a transparent tubular member, made of glass or quartz and having one end closed and the other end formed with an opening 1a and, is formed to have, for example, an inner diameter size of 0.4 to 4 mm and a length dimension of 10 to 30 mm. Then, the semipermeable membrane 2 is inserted into the sealed container 1, and the opening 1*a* is airtightly sealed by the sealing member 4.

Here, the semipermeable membrane 2 is a bag-like membrane made of a material with a molecular weight cut-off that is in the range of 2,000 to 100,000 Da and inhibits passage of the protein while allowing passage of the precipitant, and the semipermeable membrane 2 is formed in an elongated bag-like shape with an outer diameter size of 0.2 to 0.4 mm, for example.

As the semipermeable membrane 2, it is possible to use: regenerated cellulose membranes (RC) such as cuprammonium rayon (CR) and saponified cellulose (SCA); surface-modification regenerated cellulose membranes such as a hemophan membrane, a PC membrane, and a vitamin E-coating membrane; cellulose acetate (CA) such as cellulose diacetate (CDA) and cellulose triacetate (CTA); and synthetic polymer membranes such as polyacrylonitrile (PAN), polymethylmethacrylate (PMMA), an ethylene vinyl alcohol copolymer (EVAL), polysulfone (PS), polyamide (PA), and polyester polymer alloy (PEPA).

Further, the opening of the semipermeable membrane 2 is integrated with a tubular narrow tube 5. Specifically, the periphery of the opening of the semipermeable membrane 2 is inserted into the narrow tube 5 and integrated therewith by using the adhesive 5*a*. As the narrow tube 5, a metal tube, a plastic tube, a glass tube, a quartz tube, or the like can be used.

Then, the full-length semipermeable membrane 2 and a part of the narrow tube 5 are inserted into the sealed container 1, and the sealing member 4 for closely sealing the sealed container 1 is provided on the outer periphery of the opening end of the sealed container 1 and the outer periphery of the narrow tube 5 which protrudes from the sealed container 1.

The sealing member 4 is configured of: cylindrical silicone rubber (elastic member) 6 having a hole 6*a* formed in the center, the hole 6*a* having a diameter smaller than the outer diameters of the sealed container 1 and the narrow tube 5; and a cylindrical restraint tube 7 made of metal and having an inner diameter size smaller than the outer diameter size of the silicone rubber 6.

The restraint tube 7 is formed to have an inner diameter size of 4.5 to 4.9 mm and a length dimension of 8 to 12 mm. The silicone rubber 6 has a hardness of 15 to 25 degrees and is formed to have an outer diameter in the range of 1.1 to 1.9 when the inner diameter of the restraint tube 7 is 1, specifically, an outer diameter size of 5 to 6 mm and a length dimension of 6 to 10 mm.

For sealing the opening 1*a* of the sealed container 1 with the sealing member 4, first, the silicone rubber 6 is compressed and fitted into the restraint tube 7, and then, the hole 6*a* of the silicone rubber 6 is pushed to be widened and the opening end of the sealed container 1 is inserted and fitted into the hole 6*a*. Subsequently, the hole 6*a* is pushed to be widened from the other end side of the silicone rubber 6, the narrow tube 5 having the semipermeable membrane 2 at the tip is caused to pass through the hole 6*a*, and the narrow tube 5 is pushed 3 to 7 mm into the silicone rubber 6 while the semipermeable membrane 2 is disposed in the sealed container 1.

As a result, the opening 1*a* of the sealed container 1 and the outer periphery of the narrow tube 5 are sealed with the silicone rubber 6, and the space between the outer periphery of the silicone rubber 6 and the restraint tube 7 is sealed.

The precipitant supply means 3 for circulating and supplying the precipitant solution into the semipermeable membrane 2 is connected to the narrow tube 5.

The supply means 3 is configured of: a reservoir 8 that stores the precipitant solution; a circulation line 10 made up of a tube 10*a* that supplies the precipitant solution in the reservoir 8 into the semipermeable membrane 2 by using a pump 9 and a tube 10*b* that returns the precipitant solution in the semipermeable membrane 2 back into the reservoir 8; and a port (concentration adjustment means) 11 that is provided above the reservoir 8 and supplies the precipitant solution with a different concentration into the reservoir 8 to change the precipitant concentration in the precipitant solution.

Here, when the reservoir 8 is small in volume relative to the volume of the sealed container 1, the concentration and/or pH of the precipitant in the reservoir 8 are affected by the precipitant concentration in the protein solution, and the concentration becomes unstable. Hence the volume of the reservoir 8 is preferably 100 times or more the volume of the sealed container 1 and is set to be 1 to 50 mL in the present embodiment in consideration of the viewpoint of handling. Note that reference numeral 12 in the figure denotes power supply equipment for driving and controlling the pump 9.

Next, a description will be given of a first embodiment of the protein crystallization method according to the present invention using the protein crystallization device having the above configuration.

The sealed container 1 is previously filled with a protein solution having a predetermined concentration, the opening 1*a* is sealed with the sealing member 4, and a precipitant solution adjusted to have a predetermined concentration and stored in the reservoir 8 is continuously circulated from the tube 10*a* via the semipermeable membrane 2 by the pump 9 and from the tube 10*b* to the reservoir 8.

Here, the precipitant may be salt or polymer that can be condensed without modifying the protein, and in general, sodium chloride, ammonium sulfate, polyethylene glycol, or the like can be used.

When the precipitant solution is continuously circulated, the precipitant infiltrates from the semipermeable membrane 2 into the sealed container 1 since the semipermeable membrane 2 is formed of the material that inhibits passage of the protein while allowing passage of the precipitant. Therefore, when the circulation supply to the semipermeable membrane 2 described above is performed while the precipitant solution with a high concentration is gradually supplied from the port 11 into the reservoir 8, the protein is crystallized at the time when the precipitant concentration in the sealed container 1 reaches a predetermined concentration.

Then, the crystallization is observed from the outside of the transparent sealed container 1, and the concentration and/or pH of the precipitant at that time are confirmed, so that it is possible to grasp the protein crystallization conditions.

As described above, according to the protein crystallization device and the crystallization method using this device, with respect to the solution of protein having filled the transparent sealed container 1, the precipitant solution with the changed concentration and/or pH of the precipitant is continuously supplied to the semipermeable membrane 2 disposed in the sealed container 1 via the sealing member 4, to gradually change the concentration and/or pH of the precipitant infiltrating from the semipermeable membrane 2 into the sealed container 1 and crystallize the protein, so that it is possible to crystallize the protein without changing the concentration of the protein.

In this case, due to the sealed container 1 being transparent, it is possible, by observing the crystallization of the protein from the outside, to grasp conditions of the concentration and/or pH of the precipitant at the time of protein crystallization from the fact of the protein crystallization and the concentration and/or pH of the precipitant at the time of the crystallization. Therefore, it is possible to efficiently find conditions for the crystallization by using a small amount of protein. Further, by using a glass tube or a quartz tube for the sealed container 1, the generated protein can be directly used for X-ray diffraction or neutron diffraction without being transferred to an analysis container.

In addition, the narrow tube 5 integrated to the opening end of the sealed container 1 and the semipermeable membrane 2 is fitted to the hole 6a of the silicone rubber 6, and the silicone rubber 6 is compressed by the restraint tube 7, so that by the repulsive force of the silicone rubber 6, the spaces between the hole 6a of the silicone rubber 6, the opening end of the sealed container 1, and the outer periphery of the narrow tube 5 are sealed, and the space between the outer periphery of the silicone rubber 6 and the restraint tube 7 is sealed. Hence it is possible to obtain sealing strength high enough to withstand the difference in osmotic pressure generated between the inside and the outside of the sealed container 1.

Although the case where the sealed container 1 is filled with the protein solution has been described in the above embodiment, the present invention is not limited thereto, but it is also possible to fill the sealed container 1 with a solution containing, in addition to the protein, the precipitant having a concentration with which the protein is not crystallized.

As thus described, by previously adding a certain amount of precipitant, it is also possible to shorten the operation time until the protein crystallization, without changing the concentration of the protein.

Second Embodiment

Figure 2:
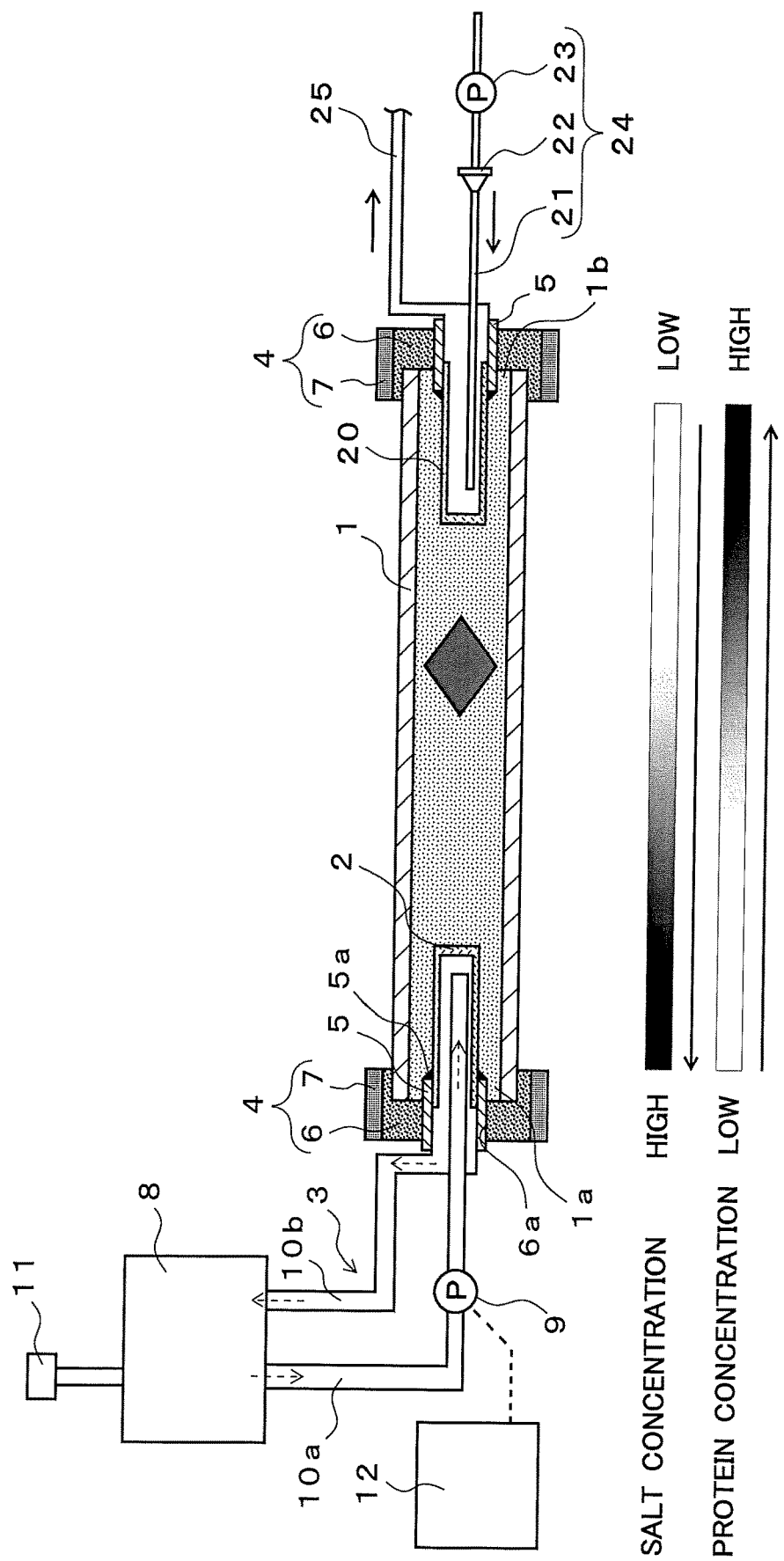
FIG. 2 is a schematic configuration view illustrating a second embodiment of the protein crystallization device according to the present invention.

FIG. 2 illustrates a second embodiment of the protein crystallization device according to the present invention, and the same components as those in the first embodiment illustrated in FIG. 1 are denoted by the same reference numerals to simplify the description thereof.

In this crystallization device, an opening 1b is formed at the other end facing the semipermeable membrane 2 of the sealed container 1, a sealing member 4 made up of the same silicone rubber 6 and restraint tube 7 is provided at the opening 1b, and a gas permeable membrane 20 extending into the sealed container 1 is provided at the tip of the narrow tube 5 inserted into the hole 6a of the silicone rubber 6.

The gas permeable membrane 20 is an elongated bag-like membrane formed of a material having a molecular weight cut-off that inhibits passage of liquid while allowing passage of water vapor, and the gas permeable membrane 20 is formed to have an outer diameter size of 0.2 to 0.4 mm, for example.

As the gas permeable membrane 20, for example, it is possible to use a membrane obtained by applying, to the surface of the semipermeable membrane 2 described above, room-temperature-vulcanizing (RTV) silicone rubber, polydimethylsiloxane (PDMS) silicone rubber, or polyurethane, which is in liquid form and has a water vapor permeability of 100 $g/m^2 \cdot 24$ h or more with use of a sample having a thickness of 25 μm in an environment of 25° C. and a relative humidity of 90% as a result of measurement by infrared sensor method described in JIS K 7129:2008.

Alternatively, it is also possible to use a membrane formed of a material, such as film-like silicone rubber, nylon (registered trademark) 6, polystyrene, or polyurethane and formed into an elongated bag-like shape of the above size.

The inside of the narrow tube 5, where the gas permeable membrane 20 is provided, is provided with: second supply means 24 made up of a filter 22, a pump 23, and a supply tube 21 that continuously supplies dry air or liquid having hygroscopic properties into the gas permeable membrane 20; and a discharge pipe (discharge means) 25 that discharges, out of the narrow tube 5, water vapor discharged out of the sealed container 1 through the gas permeable membrane 20.

Next, a description will be given of a second embodiment of the protein crystallization method according to the present invention using the protein crystallization device having the above configuration.

First, as in the first embodiment, the circulation supply to the semipermeable membrane 2 is performed while the precipitant solution with a high concentration is gradually supplied from the port 11 into the reservoir 8.

Concurrently, dry air or liquid having hygroscopic properties is continuously supplied from the supply tube 21 to the gas permeable membrane 20 disposed at the other end 1b facing the semipermeable membrane 2 of the sealed container 1, and water vapor is discharged out of the sealed container 1.

Therefore, in the sealed container 1, gradients are formed in which the concentration and/or pH of the precipitant are higher on the semipermeable membrane 2 side than on the gas permeable membrane 20 side, and the concentration of the protein is higher on the gas permeable membrane 20 side than on the semipermeable membrane 2 side. As a result, when the precipitant concentration in the sealed container 1 reaches a predetermined concentration, the crystal nuclei are generated in one to several locations, and large protein crystals are generated.

As described above, according to the protein crystallization device and the crystallization method using this device, as in the first embodiment, the crystallization is observed from the outside of the transparent sealed container 1, and the concentration and/or pH of the precipitant at that time are confirmed, so that it is possible to roughly grasp the protein crystallization conditions and further to generate large protein crystals in the sealed container 1.

EXAMPLES

Example 1

In order to verify the sealing strength of the sealing member described above, the following experiment was carried out.

First, silicone rubber with an outer diameter of 6 mm and a length of 8 mm was pushed into a restraint tube with an inner diameter of 4.7 mm and a length of 10 mm, and a narrow tube integrated at the tip with a semipermeable membrane with an outer diameter of 0.24 mm and a length of 1 mm was caused to pass through the silicone rubber. The space between the narrow tube and the silicone rubber was sealed, and further, the semipermeable membrane was inserted into a glass tube (corresponding to a sealed container) with an inner diameter of 0.4 mm and an outer diameter of 1.2 mm. The glass tube was inserted 5 mm into the silicone rubber, and the space between the glass tube and the silicone rubber was sealed.

Then, a pressure gauge and a syringe were attached to the other end of the glass tube and pressurization was performed using the syringe, to confirm that the sealing member has a pressure resistance of 250 kPa. This indicates that the sealing member can withstand the concentration difference up to about 100 mM.

Example 2

Next, in order to verify the effectiveness of the protein crystallization method according to the present invention, the following experiment was carried out.

A glass tube (corresponding to a sealed container) with an inner diameter of 1.6 mm, a length of 15 mm, and a volume of 30 μL was filled with an aqueous solution of 31.29-mg/mL lysozyme and 50-mM sodium acetate (pH 4.5). A semipermeable probe (6,000 Da cut-off) including a narrow tube and a semipermeable membrane with an outer diameter of 0.24 mm and a length of 1 mm was inserted into the glass tube, which was then sealed with silicone rubber. Thereafter, a reservoir was filled with a 5-mL aqueous solution of 50-mM sodium acetate (pH 4.5) and 0.04% sodium azide, and a pump was operated at a flow rate of 60 μL/min.

Then, after this state was held for a day, an aqueous solution of a 50-mM sodium acetate, 2,000-mM sodium chloride, and 0.04% sodium azide was gradually added into the reservoir at a flow rate of 0.62 μL/min by using a syringe pump, and the presence or absence of crystals was observed daily. As a result, when the concentration of sodium chloride in the reservoir was raised to 700-mM, lysozyme crystals, usable for X-ray diffraction, of up to 0.5 mm square were confirmed in the glass tube.

Example 3

In order to verify the effectiveness of the protein crystallization method according to the second embodiment described above, the following experiment was carried out.

A glass tube (corresponding to a sealed container) with an inner diameter of 1.6 mm, a length of 15 mm, and a volume of 30 μL was filled with an aqueous solution of 50-mM lysozyme and 50-mM sodium acetate (pH 4.5) and an aqueous solution of 5% PEG 4000. A semipermeable probe (6,000 Da cut-off) including a narrow tube and a semipermeable membrane with an outer diameter of 0.24 mm and a length of 1 mm was inserted into the glass tube, which was then sealed with silicone rubber. Meanwhile, from the other end side, a gas permeable membrane probe, obtained by applying RTV silicone to the outer side of the semipermeable membrane, was inserted into the glass tube, which was then sealed with silicone rubber.

Subsequently, a reservoir was filled with a 5-mL aqueous solution of 50-mM sodium acetate (pH 4.5) and 5% PEG 4000, and a pump was operated at a flow rate of 0.2 μL/min. After this state was held for a day, an aqueous solution of 50-mM sodium acetate, 2,000-mM sodium chloride, and 5% PEG 4000 was gradually added by a syringe pump into the reservoir at a flow rate of 0.2 μL/min, and air started to be fed at a flow rate of 0.5 μL/min into a gas permeable membrane probe coated with RTV silicone, and this state was held for four days so that the concentration of sodium chloride is 0.4 M. Then, 3.75-mL was added at a flow rate of 0.4 μL/min.

As a result, a total of three crystals were generated in the glass tube, and lysozyme crystals of up to 1.8 mm square were obtained. Then, X-ray diffraction was performed and the resolution and orientation of the crystals were measured, to confirm that the crystals have good quality.

INDUSTRIAL APPLICABILITY

The present invention can provide an economically superior protein crystallization method capable of efficiently finding conditions for crystallization by using a small amount of protein and provide a crystallization device used for the method.

REFERENCE SIGNS LIST 1 sealed container
2 semipermeable membrane
3 precipitant supply means
4 sealing member
5 narrow tube
6 silicone rubber (elastic member)
7 restraint tube
8 reservoir
9 pump
11 port (concentration adjustment means)
20 gas permeable membrane
24 second supply means
25 discharge tube (discharge means)

The invention claimed is:

1. A protein crystallization method comprising:
filling a transparent sealed container with a solution of protein, a part of the transparent sealed container being formed of a semipermeable membrane with a molecular weight cut-off that inhibits passage of the protein while allowing passage of a precipitant; and
continuously supplying a precipitant solution to the semipermeable membrane while changing concentration and/or pH of the precipitant in the precipitant solution, and circulating the precipitant solution at the same time, to change the concentration and/or pH of the precipitant infiltrating from the semipermeable membrane into the sealed container, and to crystallize the protein with the precipitant that infiltrates from the semipermeable membrane into the sealed container.

2. The protein crystallization method according to claim 1,
wherein dry air or liquid having hygroscopic properties is continuously supplied to a gas permeable membrane disposed in a position that faces the semipermeable membrane of the sealed container and having a molecular weight cut-off that inhibits passage of liquid while allowing passage of water vapor, to form gradients of the concentration and/or pH of the precipitant and a concentration of the protein in the sealed container.

3. The protein crystallization method according to claim 1, wherein the solution with which the sealed container is filled contains, in addition to the protein, the precipitant having a concentration with which the protein is not crystallized.

4. A protein crystallization device comprising:
a transparent sealed container filled with a solution containing protein;
a semipermeable membrane that forms a part of the sealed container and inhibits passage of the protein while allowing passage of a precipitant; and
precipitant supply means that circulates and supplies a precipitant solution containing the precipitant to the semipermeable membrane, wherein the precipitant supply means includes
a reservoir that stores the precipitant solution,
a circulation line that supplies the precipitant solution in the reservoir to the semipermeable membrane and returns the precipitant solution to the reservoir again,
a pump that is disposed on the circulation line and continuously supplies the precipitant solution to the semipermeable membrane, and
concentration adjustment means that changes the precipitant concentration in the precipitant solution.

5. The protein crystallization device according to claim 4, wherein
the sealed container is a tubular member having one end closed and the other end formed with an opening,
the semipermeable membrane is formed in a bag-like shape integrated at the opening with a cylindrical narrow tube and is inserted into the sealed container via a sealing member,
the sealing member includes
a cylindrical elastic member having a hole formed in a center, the hole having a diameter smaller than outer diameters of the sealed container and the narrow tube, and
a cylindrical restraint tube having an inner diameter size smaller than an outer diameter size of the elastic member, and
the sealed container is fitted to one end of the hole in the elastic member while the narrow tube is fitted to the other end of the hole, and the compressed elastic member is fitted into the restraint tube.

6. The protein crystallization device according to claim 4, comprising:
a gas permeable membrane disposed in a position that faces the semipermeable membrane of the sealed container and having a molecular weight cut-off that inhibits passage of liquid while allowing passage of water vapor;
second supply means that continuously supplies dry air or liquid having hygroscopic properties to the gas permeable membrane; and
discharge means for water vapor discharged out of the sealed container through the gas permeable membrane.

7. The protein crystallization device according to claim 4, wherein the sealed container is made of glass or quartz.

8. The protein crystallization device according to claim 5, wherein the elastic member is silicone rubber with a hardness of 15 degrees to 25 degrees.

* * * * *